United States Patent [19]

Kamei

[11] Patent Number: 5,141,608
[45] Date of Patent: Aug. 25, 1992

[54] PROCESS OF PREPARING 2-CHLOROPYRIDINE AND/OR 2,6-DICHLOROPYRIDINE

[75] Inventor: Noboru Kamei, Arai, Japan

[73] Assignee: Daicel Chemical Industries, Ltd., Sakai, Japan

[21] Appl. No.: 719,669

[22] Filed: Jun. 24, 1991

Related U.S. Application Data

[63] Continuation of Ser. No. 252,574, Sep. 30, 1988, abandoned.

[30] Foreign Application Priority Data

Oct. 9, 1987 [JP] Japan .................. 62-256104

[51] Int. Cl.$^5$ .............................................. B01J 1/10
[52] U.S. Cl. .............................................. 204/157.71
[58] Field of Search ............... 204/157.48, 157.86, 204/157.71; 546/345

[56] References Cited

U.S. PATENT DOCUMENTS

| | | | |
|---|---|---|---|
| 3,186,994 | 6/1965 | Johnston | 546/345 |
| 3,251,848 | 5/1966 | Taplin | 546/345 |
| 3,297,556 | 1/1967 | Boudakian et al. | 204/157.71 |
| 3,969,205 | 7/1976 | Kawamura | 204/157.71 |
| 4,071,521 | 1/1978 | Muench | 546/345 |
| 4,256,894 | 3/1981 | Dietsche | 546/345 |
| 4,752,644 | 6/1988 | Sharvit | 546/345 |

FOREIGN PATENT DOCUMENTS

| | | | |
|---|---|---|---|
| 1445683 | 1/1969 | Fed. Rep. of Germany | 546/345 |
| 154266 | of 1975 | Japan . | |

*Primary Examiner*—John Niebling
*Attorney, Agent, or Firm*—Flynn, Thiel, Boutell & Tanis

[57] ABSTRACT

2-chloropyridine and/or 2,6-dichloropyridine are effectively produced by reacting pyridine with chlorine gas in the gaseous phase with irradiation of ultraviolet rays, while the reaction gas mixture is being agitated.

4 Claims, No Drawings

PROCESS OF PREPARING 2-CHLOROPYRIDINE AND/OR 2,6-DICHLOROPYRIDINE

This application is a continuation of U.S. Ser. No. 07/252,574, filed Sep. 30, 1988, now abandoned.

FIELD OF THE INVENTION

This invention relates to an improved process of preparing 2-chloropyridine and/or 2,6-dichloropyridine from pyridine and chlorine by photochemical reaction. They are useful as intermediates for manufacturing medicines and agricultural chemicals.

DESCRIPTION OF THE PRIOR ART

Numerous methods for preparing 2-chloropyridine and/or 2,6-dichloropyridine by reacting pyridine and chlorine in the gaseous phase containing them under irradiation of ultraviolet light have been already known. These, however, from the viewpoint of long-lasting stable reaction operation important for production on an industrial scale, encounter the following problem.

Reaction of pyridine and chlorine in the absence of any other substance is accompanied by formation of tarry products associated with pyridine-chlorine complex, as causes for staining the lamp and for causing clogging of the reaction product outlet, etc. Thus, long-lasting stable reaction operation can be accomplished with difficulty.

A method for avoiding the difficulty, which method used carbon tetrachloride as a diluent, was disclosed in U.S. Pat. No. 3,297,556. This is disadvantageous in that a by-product pyridine hydrochloric acid deposits onto the lamp, causing lowered lamp efficiency. Other improvements were disclosed in Japanese Patent Publication Nos. 3935/1977, 3936/1977 and 4742/1980 in which at least one mole of water vapor or halogenated hydrocarbon-water vapor is added to pyridine.

These methods however, have the disadvantage of being incapable of obtaining efficiency even as small low as about 30%. In order to yield 2,6-dichloropyridine as a major product, reaction is conducted in an increased molar ratio of chlorine to pyridine. For example, when the molar ratio is 2, one-half the total of chlorine remains unreacted and is contained in the discharge gas, with result that a low conversion of pyridine occurs, for example, as low as 50%.

As described above, when considerable amounts of pyridine and chlorine gas used remain unreacted, many problems arise:

Firstly, unreacted pyridine is condensed in the gas discharging line, and there it reacts with hydrochloric acid gas to be converted into pyridine hydrochloric acid, which starts to separate as crystals, with the consequence of difficulty caused by beginning of clogging. When a large amount of gas is discharged, a not negligible loss of pyridine occurs because the discharged gas includes unreacted pyridine. Since a good recovery cannot be expected because of the complexity of the subsequent handling steps of the excess amount of material, it is believed to be important for stable operation of the process to increase the conversion of pyridine and the reaction proportion of chlorine gas.

Use of a smaller amount of a diluent, such as water or carbon tetrachloride, to accelerate the reaction results in prevailing side reactions, such as polymerization of pyridine. Operation at reaction temperatures exceeding 200° C. is difficult, taking the material of which reaction apparatus is made into consideration. In this way the inventors were driven to search for countermeasures for accelerating substantially the reaction.

SUMMARY OF THE INVENTION

Under the circumstances, the inventor's work has been done intensely to solve the above-mentioned problems, and the present invention has been accomplished with the resulting surprising finding that agitation of the gaseous phase to full intermixing by work of an agitator, or the like, brought about a great improvement in reaction rate.

The present invention is concerned with a process of preparing 2-chloropyridine and/or 2,6-dichloropyridine comprising reacting pyridine and chlorine in the gaseous phase consisting of pyridine vapor and chlorine gas under irradiation of ultraviolet rays while agitating the gaseous phase to full intermixing.

In the invention, 2-chloropyridine and/or 2,6-dichloropyridine are effectively produced by reacting pyridine with chlorine gas in the gaseous phase with irradiation of ultraviolet rays, while the reaction gas mixture is being agitated.

It is preferred that the agitation is effected so that a resulting, apparent flow rate may be increased 2.4 times as much as that with no agitation. The agitation may be carried out with a blower to circulate the reaction gas mixture or with an agitator.

In the gas phase photochemical reactor, generally the residence time therein is selected to be in the range of 10 to 40 seconds where it has been believed that pyridine vapor and chlorine gas become fully intermixed. Rather, taking the sequential reaction into consideration, a plug flow (cylinder) type reactor is used.

The inventors have found that the mounting of an agitator in the reaction apparatus for analyzing the reaction rate affected caused the reaction to markedly accelerate. Apparatus like this easily gave a conversion of 90% or more and maintained the reaction proportion of chlorine at 90% or more. Such remarkable accelerating effect of agitation of the gaseous phase on the reaction was by far beyond expectation.

Agitation of gaseous material in a reaction apparatus can be carried out with an agitator, and other means, for example, by external (relative to the apparatus) circulation of gaseous material in the apparatus under the work of a blower, or by the stepwise injection of chlorine or a diluent gas, such as nitrogen, into the apparatus. It is direct mixing with an agitator in the apparatus that is the most preferred.

In view of the fact that mere feeding of gaseous material into the reaction apparatus effects inadequate mixing of them, the intention of the present invention resides in conducting forced agitation whatever technique may be used.

In detail, gaseous material is fed under such forced agitation into the reaction apparatus that at the reaction temperature the apparent flow "Fa" of gaseous material is 2.4 or more times that without forced agitation, as expressed in the following equation:

$$Fa \geq 2.4 \, V/t$$

wherein V is volume of the reaction apparatus, and t is residence time, thus $V/t$ implying flow of gaseous material at the reaction temperature.

This means, for example, external circulation under the work of a blower should be carried out at not less than 2.4 times more flow than feeding flow without agitation.

When agitation in the reaction apparatus is conducted with an agitator, similarly the condition is defined as follows:

$N \geq 30/t$ wherein N is the number of revolutions when a conventional agitation blade is used. For example, assuming t=40 seconds, it follows that $N \geq 0.75$ rps $\geq 45$ rpm.

In practice, the number of revolutions N is preferred to be at least 200 rpm, depending on the type of agitation blade. The upper limit of the number of revolutions is not specified, and commercially-available agitators having the number of revolutions between 1200 and 1500 can be adequately used.

The agitating blade is preferred to have a large area to the agitating effect, since it serves in the gaseous phase. Any blade can be used, such as turbine type, Pfaudler type and propeller type.

For the reaction, adequate residence time in the reaction apparatus is between 10 to 30 seconds. By prolongation of residence time exceeding the range, the reaction is unaffected, and therefore added amounts of material can be changed as desired. A molar ratio of pyridine to chlorine can be set differently in accordance with what molar ratio of 2-chloropyridine and 2,6-dichloropyridine in reaction mixture should is desired.

Suitable reaction temperatures are 120° C. or higher, preferably 140° C. or higher. Reaction rate increases with higher reaction temperature, though it is generally limited to 200° C. from the problem involving the material of which the reactor is made.

A diluent is added to prevent the U. V. lamp from becoming dirty and to reduce tarring of pyridine, and typical examples of it include water, carbon tetrachloride and nitrogen gas. The conventional process, owing to slow reaction, does not permit a high dilution while in the present process, no problems arise if the amount of dilution is 20 or more moles per mole of pyridine. Usually the used amount of diluent is 10 to 30 mole times that of pyridine.

Reaction mixture is passed through a condenser of which the cooling medium is warm water to be condensed and led to a receiver with a gas discharging line.

The resulting reaction solution is neutralized with sodium hydroxide, extracted with carbon tetrachloride and a simple fractional distillation to obtain the intended chemicals.

The process according to the invention, 2-chloropyridine or 2,6-dichloropyridine provide yields as much as several times more than the conventional technology, while enabling long-lasting stable operation with no occurrence of troubles such as clogging.

The invention will be described more fully by way of Examples hereinafter:

EXAMPLE 1

A 5-liter pyrex jacketed photochemical reaction apparatus having necks or ports each for fitting with a lamp, an agitator and a thermometer, respectively, a gas inlet, and a gas outlet was employed. As light source a 100 W high pressure mercury arc lamp was used.

The lamp was located at substantially the center of the apparatus. Around the lamp, a concave Teflon agitator was mounted and operated to run at 200 rpm.

To the apparatus which was heated to an inside temperature of 130° C., pyridine (900 g/H), water (410 g/H) and chlorine gas (121 g/H) were fed.

During the reaction, the temperature of the apparatus was kept at 160° C. through the control of heat transfer medium temperature.

Gaseous reaction product was condensed by the pass through a warmed-water condenser and pooled in a 1-liter receiver containing the circulated warmed water. Intermittent drawing out of the solution from the receiver was carried out. Reaction solution was obtained at a rate of 612 g/H, of which pyridine 5.4 g/H, 2-chloropyridine 62.1 g/H, and 2,6-dichloropyridine 74.7 g/H were found. As calculated out from these, conversion of pyridine was 94%, and proportions of 2-chloropyridine and 2,6-dichloropyridine were 51.1% and 47.1%, respectively. The degree of reaction of chlorine gas fed was 92.6%.

During 24 hours' continuous operation, there occurred no troubles which would result if the discharge gas cooler attached to the receiver and the gas outlet from there got clogged.

EXAMPLE 2

The same procedure as in Example 1 was repeated except that 88 g/H of chlorine was fed. The reaction solution was obtained at a rate of 620 g/H, including unreacted pyridine at 14.8 g/H, 2-chloropyridine at 80.6 g/H, and at 2,6-dichloropyridine at 34.0 g/H.

As calculated out from these, conversion of pyridine was 83.6%, and proportions of 2-chloropyridine and 2,6-dichloropyridine were 74.6% and 24.1%, respectively. The degree of reaction of chlorine gas fed the system was 95.5%.

EXAMPLE 3

The procedure of Example 2 was employed with the exception that water was fed at an increased rate of 513 g/H to obtain a reaction solution at a rate of 721 g/H including unreacted pyridine at 15.2 g/H, 2-chloropyridine at 82.5 g/H, and 2,6-dichloropyridine at 30.7 g/H.

As calculated out from these, conversion of pyridine was 83.1%, and proportions of 2-chloropyridine and 2,6-dichloropyridine were 76.8% and 21.9%, respectively. The degree of reaction of chlorine gas fed was 91.9%.

EXAMPLE 4

The procedure of Example 1 was repeated with the exception that the addition of water at a rate of 10 g/H, followed by nitrogen at a rate of 50 g/H. Besides, water was fed to a liquid reaction product receiver at a rate of 500 g/H, and the solution of the receiver was pumped to circulate for direct quenching of the reaction gas.

There was obtained a reaction solution including unreacted pyridine at 1.1 g/H, 2-chloropyridine at 63.8 g/H, and 2,6-dichloropyridine at 79.8 g/H. As calculated from these, conversion of pyridine was 98.8%, and proportions of 2-chloropyridine and 2,6-dichloropyridine were 50.0% and 47.9%, respectively.

CONTROL EXAMPLE 1

This example was carried out without using an agitator, and the other conditions were the same as in Example 2, and the results were obtained: reaction solution and discharge gas included unreated pyridine at 66.2 g/H, 2-chloropyridine at 11.0 g/H, and 2,6-dichloropyridine at 24.1 g/H. As calculated out from these, conversion of pyridine was 26.4%, and absorption of chlorine gas was only 39%.

Besides during 12 hours' operation, airing condenser and gas discharging ports frequently got clogged associated with deposition of crystals onto them.

I claim:

1. A process for preparing 2-chloropyridine and/or 2,6-dichloropyridine, which comprises: in a reactor, reacting pyridine vapor and chlorine gas, in the presence of at least 20 moles of a diluent per mole pyridine, at a temperature in the range of from about 120° C. to about 200° C. under ultraviolet radiation; simultaneously mixing and stirring said pyridine vapor and chlorine gas inside said reactor by means of a rotating, mechanical impeller located inside said reactor to effect full and uniform intermixing throughout said reactor, said impeller being rotated at an rpm (N) which satisfies the relation $N \geq 30/t$, wherein t is the residence time (min.) of said vapor and said gas in said reactor and N is from about 45 to about 1,500 rpm; and then recovering 2-chloropyridine and/or 2,6-dichloropyridine.

2. A process as claimed in claim 1 in which N is at least about 200 rpm and t is at least about 1/6 minute.

3. A process for preparing 2-chloropyridine and/or 2,6-dichloropyridine, which comprises: in a reactor, reacting pyridine vapor and chlorine gas, in the presence of at least 20 moles of a diluent per mole pyridine, at a temperature in the range of from about 120° C. to about 200° C. under ultraviolet radiation; continuously withdrawing a portion of said pyridine vapor and chlorine gas from one portion of said reactor and returning it to a different portion of said reactor, whereby full intermixing is achieved throughout said reactor and in which the following relation is satisfied $Fa \geq 2.4 V/t$, wherein Fa is the apparent volumetric flow rate of said vapor and said gas in said reactor, V is the volume of said reactor and t is the residence time of said gas and said vapor in said reactor and is from about 10 to about 40 seconds; and recovering 2-chloropyridine and/or 2,6-dichloropyridine.

4. A process as claimed in claim 3 in which said vapor and said gas are circulated through said reactor by means of a blower located outside said reactor.

* * * * *